(12) United States Patent
Chen et al.

(10) Patent No.: US 6,664,261 B2
(45) Date of Patent: *Dec. 16, 2003

(54) PYRAZOLOPYRIMIDINES AS CRF RECEPTOR ANTAGONISTS

(75) Inventors: Chen Chen, San Diego; Thomas R. Webb, Olivenhain; James R. McCarthy, Solana Beach; Terence J. Moran, San Diego; Keith M. Wilcoxen, Groton Long Point; Charles Huang, San Diego, all of CA (US)

(73) Assignee: Neurocrine Biosciences, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,717

(22) PCT Filed: Jan. 30, 1997

(86) PCT No.: PCT/EP97/00459

§ 371 (c)(1),
(2), (4) Date: Mar. 2, 1999

(87) PCT Pub. No.: WO97/29109

PCT Pub. Date: Aug. 14, 1997

(65) Prior Publication Data

US 2003/0125341 A1  Jul. 3, 2003

Related U.S. Application Data

(60) Provisional application No. 60/011,279, filed on Feb. 7, 1996, and provisional application No. 60/027,688, filed on Oct. 8, 1996.

(51) Int. Cl.⁷ .................... A61K 31/505; C07D 239/00; C07D 487/00
(52) U.S. Cl. .................... 514/258; 544/250; 544/281
(58) Field of Search .................... 514/258; 544/250, 544/281

(56) References Cited

U.S. PATENT DOCUMENTS

| | | | |
|---|---|---|---|
| 3,920,652 A | 11/1975 | Springer et al. | 260/256.4 |
| 4,021,556 A | 5/1977 | Springer et al. | 424/251 |
| 5,420,128 A | 5/1995 | Kiyokawa et al. | 514/246 |
| 5,571,813 A | 11/1996 | Ruhter et al. | 514/257 |
| 5,688,949 A | * 11/1997 | Inoue et al. | 544/281 |
| 5,707,997 A | 1/1998 | Shoji et al. | 514/258 |
| 5,843,951 A | * 12/1998 | Inoue et al. | 514/258 |
| 5,985,882 A | 11/1999 | Inoue et al. | 514/256 |
| 2002/0151713 A1 | 10/2002 | Chen | |

FOREIGN PATENT DOCUMENTS

| | | |
|---|---|---|
| EP | 0244 097 A2 | 11/1987 |
| EP | 0 691 128 A1 | 1/1996 |
| EP | 591 528 B1 | 12/1998 |
| JP | 42-11753 | 7/1967 |
| JP | 44-30512 | 12/1969 |
| JP | 45-30335 | 10/1970 |
| JP | 61-57587 | 3/1986 |
| JP | 3-204877 | 9/1991 |
| WO | WO 94/13676 | 6/1994 |
| WO | WO 94/13677 | 6/1994 |
| WO | WO 95/33750 | 12/1995 |
| WO | WO 96/28448 | 9/1996 |
| WO | WO 96/35689 | 11/1996 |

OTHER PUBLICATIONS

Japan Abstract Publication No. 05017470, dated Jan. 26, 1993.
Japan Abstract Publication No. 07309872, dated Nov. 28, 1995.
Japan Abstract Publication No. 08003167, dated Sep. 1, 1996.
Chem. Abstract, vol. 67, No. 23, Dec. 4, 1967, Abstract No. 108663R.

(List continued on next page.)

*Primary Examiner*—Richard L. Raymond
*Assistant Examiner*—Tamthom N. Truong
(74) *Attorney, Agent, or Firm*—Seed IP Law Group PLLC

(57) ABSTRACT

This invention concerns compounds of formula

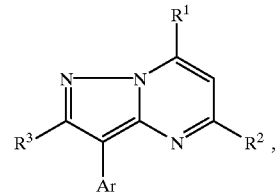

(I)

including the stereoisomers and the pharmaceutically acceptable acid addition salt forms thereof, wherein $R^1$ is $NR^4R^5$ or $OR^5$; $R^2$ is $C_{1-6}$alkyl, $C_{1-6}$alkyloxy or $C_{1-6}$alkylthio; $R^3$ is hydrogen, $C_{1-6}$alkyl, $C_{1-6}$alkylsulfonyl, $C_{1-6}$alkylsulfoxy or $C_{1-6}$alkylthio; $R^4$ is hydrogen, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl; $R^5$ is $C_{1-6}$alkyl, mono- or di($C_{3-6}$cycloalkyl)methyl, $Ar^1CH_2$, $C_{1-6}$alkyloxy$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of formula —Alk—O—CO—$Ar^1$; or $R^4$ and $R^5$ taken together with the nitrogen atom to which they are attached may form an optionally substituted pyrrolidinyl, piperidinyl, homopiperidinyl or morpholinyl group; having CRF receptor antagonistic properties; pharmaceutical compositions containing such compounds as active ingredients; methods of treating disorders related to hypersecretion of CRF such as depression, anxiety, substance abuse, by administering an effective amount of a compound of formula (I).

14 Claims, No Drawings

OTHER PUBLICATIONS

Chem. Abstract, vol. 105, No. 25, Dec. 22, 1996, Abstract No. 226617e.

Derwent Abstract, Japanese Patent No. 61–57587.

Derwent Abstract, Japanese Patent No. 44–30512, 2000.

Auzzi et al. (1983) "2–Phenylphyrazolo [1,5–a] pyrimidin–7–ones. A new Class of Nonsteroidal Antinflammatory Drugs Devoid of Ucerogenic Activity", J. Med. Chem., vol. 26, pp. 1706–1709.

Bruni et al. (1993) "Synthesis and Study of the Anti–Inflammatory Properties of Some Pyrazolo [1,5–a] pyrimidine Derivatives", Journal of Pharmaceutical Sciences, vol. 82, No. 5.

Ibrahim, et al. (1987) "Synthesis of New 3—(Pyridin–6–yl) pyrazolo [1,5a]n pyrimidines", Arch. Pharm. (Weinheim) 320. 487–491 (1987).

Joshi, et al. (1979) "Synthesis of Some New Fluorine Containing Pyrazolo [1,5a] pyrimidines", *Journal f.prakt.Chemie. Band 321, Heft 2, 1979, S. 341–344.*

Novinson, et al. (1976) "Novel Heterocyclic Nitrofurfal Hydrazones. In Vivo Antitrypanosomal Activity" *Journal of Medicinal Chemistry*, vol. 19, No. 4, pp. 512–1516.

Senga, et al. (1981) "Synthesis and Antishistosomal Activity of Certain Pyrazolo [1,5–a] pyrimidines", *J. Med. Chem*, vol. 24, pp. 610–613.

Springer, et al. (1976) "Synthesis and Enzymic Activity of Some Novel Xanthine Oxidasse Inhibitors. 3–Substituted 5, 7–Dihydroxypyrazolo [1,5–a] pyrimidines" *Journal of Medicinal Chemistry*, vol. 19, No. 2, pp. 291–296.

Journal of Medicinal Chemistry, 1977 vol. 20, No. 3 Novinson et al. 386–393.

Derwent Abstract of JP 61–57587—Acc No. 1986–116678, 1998.*

Abstract of Japanese Application No. 45–30335, 1991.

Abstract of Japanese Application No. 3–204877, 1970.

* cited by examiner

PYRAZOLOPYRIMIDINES AS CRF RECEPTOR ANTAGONISTS

This application is claiming benefit of provisional applications, U.S. application Ser. No. 60/011,279, filed on Feb. 7, 1996 and U.S. application Ser. No. 60/027,688, filed on Oct. 8, 1996.

BACKGROUND OF THE INVENTION

This invention relates to pyrazolopyrimiidines which possess CRF receptor antagonistic properties, to pharmaceutical compositions containing these compounds as active ingredient, and the use thereof in the treatment of endocrine, psychiatric and neurologic conditions or illnesses, including stress-related disorders in general.

The first corticotropin-releasing factor (CRF) was isolated from ovine hypothalmi and identified as a 41-amino acid peptide (Vale et al., Science 213:1394–1397, 1981). Subsequently, sequences of human and rat CRF were isolated and determined to be identical, but different from ovine CRF in 7 of the 41 amino acid residues (Rivier et al., Proc. Natl. Acad. Sci. USA 80:4851, 1983; Shibahara et al., EMBO J. 2:775, 1983). CRF has been found to produce profound alterations in endocrine, nervous and immune system functions. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., Science 213:1394–1397, 1981). Briefly, CRF is believed to initiate its biological effects by binding to a plasma membrane receptor which has been found to be distributed throughout the brain (DeSouza et al., Science 221:1449–1451, 1984), pituitary (DeSouza et al., Methods Enzymol. 124:560, 1986; Wynn et al., Biochem. Biophys. Res. Comm. 110:602–608, 1983), adrenals (Udelsman et al., Nature 319:147–150, 1986) and spleen (Webster, E. L., and E. B. DeSouza, Endocrinology 122:609–617, 1988). The CRF receptor is coupled to a GTP-binding protein (Perrin et al., Endocrinology 118: 1171–1179, 1986) which mediates CRF-stimulated increase in intracellular production of cAMP (Bilezikjian, L. M., and W. W. Vale, Endocrinology 113:657–662, 1983).

In addition to its role in stimulating the production of ACTH and POMC, CRF is also believed to coordinate many of the endocrine autonomic, and behavioral responses to stress, and may be involved in the pathophysiology of affective disorders. Moreover, CRF is believed to be a key intermediary in communication between the immune, central nervous, endocrine and cardiovascular systems (Crofford et al., J. Clin. Invest. 90:2555–2564, 1992; Sapolsky et al., Science 238:522–524, 1987; Tilders et al., Regul. Peptides 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., Nature 297:331, 1982), persistent activation of the electroencephalogram (Ehlers et al., Brain Res. 2/8332, 1983), stimulation of the sympathoadrenomedullary pathway (Brown et al., Endocrinology 110:928, 1982), an increase of heart rate and blood pressure (Fisher et al., Endocrinology 110:2222, 1982), an increase in oxygen consumption (Brown et al., Life Sciences 30:207, 1982), alteration of gastrointestinal activity (Williams et al., Am. J. Physiol. 253:G582, 1987), suppression of food consumption (Levine et al., Neuropharmacology 22:337, 1983), modification of sexual behavior (Sirinathsinghji et al., Nature 305:232, 1983), and immune function compromise (Irwin et al., Am. J. Physiol. 255:R744, 1988). Furthermore, clinical data suggest that CRF may be hypersecreted in the brain in depression, anxiety-related disorders, and anorexia nervosa. (DeSouza, Ann. Reports in Med. Chem. 25:215–223, 1990).

Accordingly, clinical data suggest that CRF receptor antagonists may represent novel antidepressant and/or anxiolytic drugs that may be useful in the treatment of the neuropsychiatric disorders manifesting hypersecretion of CRF. CRF receptor antagonists have been reported in for example, U.S. Pat. No. 5,063,245 disclosing substituted 4-thio-5-oxo-3-pyrazoline derivatives and Australian Patent No. AU-A-41399/93, disclosing substituted 2-aminothiazole derivatives. WO-92/18504 and JP-32104877 disclose pyrazolo[1,5-a]pyrimidines as antiinflammatory agents. Also, WO-94/13676, WO-94113677 and WO-95/33750 disclose pyrrolopyrimidines, pyrazolo[3,4-d]pyrimidines and substituted purines as CRF receptor antagonists. Arylpyrazolo[1,5-a]pyrinidines have been described as xanthine oxidase inhibitors (Robins et al., J. Heterocyclic Chem. 22:601–634, 1985). JP-42/011,753 discloses 7-methylamino-pyrazolo[1,5-a]pyrimidine derivatives useful as sedative and antiphlogistic agents. And JP-61/057,587 discloses pyrazolo[1,5-a]pyrimidine derivatives useful as antiulcer agents.

Due to the physiological significance of CRF, the development of further biologically active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

DESCRIPTION OF THE INVENTION

This invention concerns CRF antagonistic compounds of formula (I)

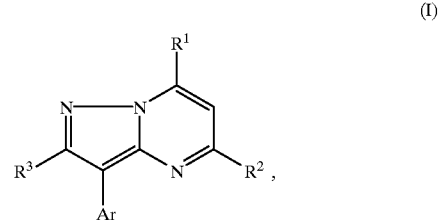

including the stereoisomers and the pharmaceutically acceptable acid addition salt forms thereof, wherein
$R^1$ is $NR^4R^5$ or $OR^5$;
$R^2$ is $C_{1-6}$alkyl, $C_{1-6}$alkyloxy or $C_{1-6}$alkylthio;
$R^3$ is hydrogen, $C_{1-6}$alkyl, $C_{1-6}$alkylsulfonyl, $C_{1-6}$alkylsulfoxy or $C_{1-6}$alkylthio;
$R^4$ is hydrogen, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl;
$R^5$ is $C_{1-8}$alkyl, mono- or di($C_{3-6}$cycloalkyl)methyl, $Ar^1CH_2$, $C_{1-6}$alkyloxy$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, morpholinyl, mono- or di($C_{1-}$ $_6$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of formula —Alk—O—CO—Ar$^1$;

or R$^4$ and R$^5$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl; and Ar is phenyl; phenyl substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl) amino; pyridinyl; pyridinyl substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino, mono- or di($C_{1-6}$alkyl)amino and piperidinyl; and wherein said substituted phenyl may optionally be further substituted with one or more halogens;

Ar$^1$ is phenyl; phenyl substituted with 1, 2 or 3 substituents each independently selected from halo, $C_{1-6}$alkyl, $C_{1-6}$alkyloxy, di($C_{1-6}$alkyl)amino$C_{1-6}$alkyl, trifluoromethyl and $C_{1-6}$alkyl substituted with morpholinyl; or pyridinyl; and Alk is $C_{1-6}$alkanediyl.

In a further aspect the invention concerns novel compounds of formula (I) as defined above, with the proviso that 5-methyl-3-phenyl-7-(phenylmethoxy)-pyrazolo[1,5-a]-pyrimidine and 2,5-dimethyl-7-(methylamino)-3-phenyl-pyrazolo[f,5-a]pyrimidine are not included The proviso is intended to exclude compounds disclosed in JP-61/057,587 and JP-42/011,753.

As used in the foregoing definitions and hereinafter, halo is generic to fluoro, chloro, bromo and iodo; $C_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof; $C_{1-2}$alkyl defines straight saturated hydrocarbon radicals having from 1 to 2 carbon atoms such as methyl and ethyl; $C_{2-4}$alkyl defines straight and branched chain saturated hydrocarbon radicals having from 2 to 4 carbon atoms such as ethyl, propyl, butyl, 1-methylethyl and the like; $C_{3-4}$alkyl defines straight and branched chain saturated hydrocarbon radicals having from 3 to 4 carbon atoms such as propyl, butyl, 1-methylethyl and the like; $C_{1-6}$alkyl includes $C_{1-2}$alkyl and $C_{3-4}$alkyl radicals as defined hereinbefore and the higher homologs thereof having from 5 to 6 carbon atoms such as, pentyl, the pentyl isomers, hexyl and the hexyl isomers; $C_{1-8}$alkyl includes $C_{1-6}$alkyl and the higher homologues thereof having from 7 to 8 carbon atoms such as, for example, heptyl, octyl and the like; $C_{3-6}$alkenyl defines straight and branched chain hydrocarbon radicals containing one double bond and having from 3 to 6 carbon atoms such as, for example, 2-propenyl, 3-butenyl, 2-pentenyl, 3-pentenyl, 3-methyl-2-butenyl, and the like; and where said $C_{3-6}$alkenyl is linked to a nitrogen or oxygen, the carbon atom making the link preferably is saturated. $C_{3-6}$cycloalkyl comprises cyclopropyl, cyclobutyl, cyclopentyl and cyclohexyl. Hydroxy$C_{1-6}$alkyl refers to $C_{1-6}$alkyl substituted with a hydroxyl-group. Homopiperidinyl refers to a 7 membered saturated ring containing one nitrogen atom.

Depending on the nature of some of the substituents, the compounds of formula (I) may contain one or more asymmetric centers which may be designated with the generally used R and S nomenclature.

The compounds of the present invention contain basic nitrogen atoms and, as such, can be present as the free base or in the form of acid addition salts, both being part of this invention. Acid addition salts may be prepared by methods well known in the art, and may be formed from organic and inorganic acids. Suitable organic acids include maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids.

Particular groups of compounds within the invention are those compounds of formula (I) wherein one or more of the following restrictions apply:

a) R$^1$ is NR$^4$R$^5$ wherein R$^4$ is hydrogen, $C_{1-6}$alkyl, hydroxy$C_{1-6}$alkyl, $C_{1-6}$alkylcarbonyloxy$C_{1-6}$alkyl or $C_{3-6}$alkenyl; in particular $C_{2-4}$alkyl, hydroxy$C_{1-2}$alkyl, $C_{3-4}$alkenyl or $C_{1-2}$alkylcarbonyloxy$C_{2-4}$alkyl; and R$^5$ is $C_{1-8}$alkyl, $C_{3-6}$alkenyl, hydroxy$C_{1-6}$alkyl, $C_{1-6}$alkyloxy$C_{1-6}$alkyl, phenylmethyl or $C_{3-6}$cycloalkylmethyl; in particular $C_{2-4}$alkyl, $C_{3-4}$alkenyl, hydroxy$C_{2-4}$alkyl or cyclopropylmethyl;

b) R$^1$ is OR$^5$ wherein R$^5$ is $C_{1-6}$alkyl; in particular $C_{2-4}$alkyl;

c) R$^2$ is $C_{1-6}$alkyl; in particular $C_{1-2}$alkyl;

d) R$^3$ is hydrogen, $C_{1-6}$alkyl or $C_{1-6}$alkylthio; in particular hydrogen, $C_{1-2}$alkyl or $C_{1-2}$alkylthio;

e) Ar is a phenyl substituted with 1, 2 or 3 substituents each independently selected from $C_{1-6}$alkyl, $C_{1-6}$alkyloxy or halo; wherein the phenyl moiety is preferably substituted in the 3-, 4-, 6-, 2,4- or 2,4,6-positions; or Ar is a pyridinyl substituted with 1, 2 or 3 substituents each independently selected from halo, amino, nitro, trifluoromethyl, mono- or di($C_{1-6}$alkyl)amino, piperidinyl or $C_{1-6}$alkyl; wherein the pyridinyl moiety preferably is connected via the 2- or 3-position to the remainder of the molecule.

Another particular group of compounds are those compounds of formula (I) wherein R$^1$ is NR$^4$R$^5$ and R$^4$ and R$^5$ are taken together with the nitrogen atom to which they are attached to form a pyrrolidinyl, piperidinyl, homopiperidinyl or morpholinyl group, optionally substituted with $C_{1-6}$alkyl or $C_{1-6}$alkyloxy$C_{1-6}$alkyl.

Preferred compounds are those compounds of formula (I) wherein R$^1$ is NR$^4$R$^5$ and R$^4$ is $C_{3-4}$alkyl or allyl, preferably propyl; R$^5$ is $C_{2-4}$alkyl, allyl or cyclopropylmethyl, preferably propyl; R$^2$ is methyl; R$^3$ is hydrogen, methyl or methylthio, preferably propyl; and Ar is a phenyl substituted with 1, 2 or 3 substituents each independently selected from halo, methyl or methoxy; and Ar in particular is pyridinyl substituted with 1, 2 or 3 substituents each independently selected from halo, methyl or dimethylamino.

More preferably Ar is 3-pyridinyl substituted in the 4- and/or 6-position with methyl or dimethylamino.

Most preferred are those compounds selected from 3-(2,4-dichlorophenyl)-5-methyl-7-(N-propyl-N-cyclopropanemethylamino)-pyrazolo[2,3-a]pyrimidine;

3-(2,4-dichlorophenyl)-5-methyl-7-(N-allyl-N-cyclopropanemethylamino)-pyrazolo[2,3-a]pyrimidine;

2-methylthio-3-(2,4-dichlorophenyl)-5-methyl-7-(N,N-diallylamino)-pyrazolo[2,3-a]pyrimidine;

2-methylthio-3-(2,4-dichlorophenyl)-5-methyl-7-(N-butyl-N-cyclopropanemethylamino)pyrazolo[2,3-a]pyrimidine;

2-methylthio-3-(2,4-dichlorophenyl)-5-methyl-7-(N-propyl-N-cyclopropanemethylamino)pyrazolo[2,3-a] pyrimidine;

2-methyl-3-(4-chlorophenyl)-5-methyl-7-(N,N-dipropylamino)-pyrazolo[2,3-a]pyrimidine;

3-[6-(dimethylamino)-3-pyridinyl]-2,5-dimethyl-N,N-dipropylpyrazolo[2,3-a]pyrimidin-7-amine; or
3-[6-(dimethylamino)-4-methyl-3-pyridinyl]-2,5-dimethyl-N,N-dipropyl-pyrazolo[2,3-a]pyrimidine-7-amine; or
3-(2,4-dimethoxyphenyl)-2,5-dimethyl-7-(N-propyl-N-methyloxyethylamino)-pyrazolo[2,3-a]pyrimidine;
the stereoisomeric forms and the pharmaceutically acceptable acid addition salts thereof.

The compounds of the present invention can generally be prepared by alkylating a pyrazolopyrimidine of formula (II) with an intermediate of formula (III). In intermediate (II), W is an appropriate leaving group such as halo, e.g. chloro, bromo, or a sulfonyloxy group, e.g. a mesyloxy or a tosyloxy group.

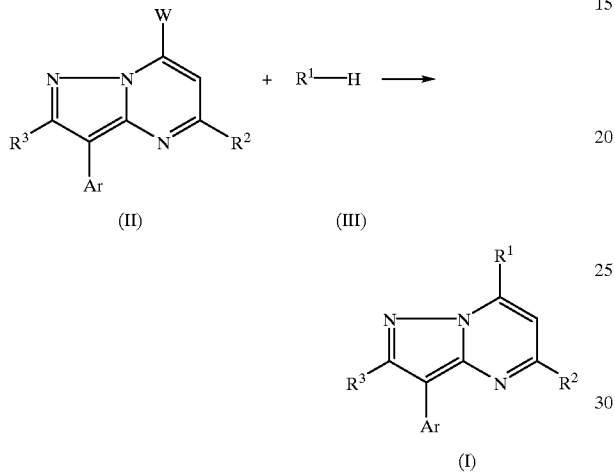

The above reaction is typically conducted in a suitable solvent, e.g. an aprotic solvent such as DMF or acetonitrile, an ether, e.g. tetrahydrofuran, preferably at an elevated temperature and, when the intermediates of formula (III) are volatile amines, in a sealed reaction vial.

Also, compounds of formula (I) wherein $R^1$ is $OR^5$, said compounds being represented by formula (I-a), may be prepared by O-alkylating an intermediate of formula (VI) with an intermediate of formula (VII), wherein W is as defined above.

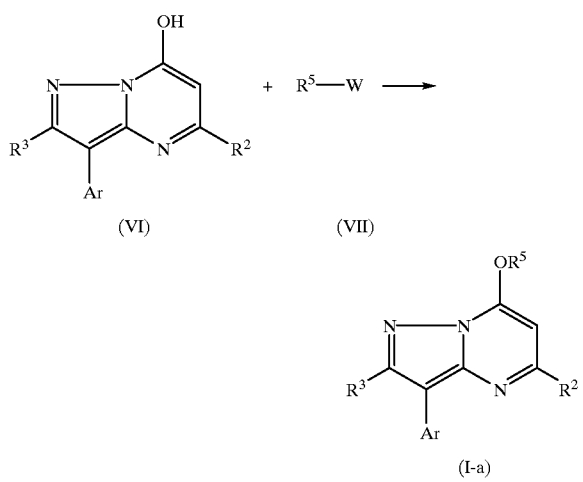

Said reaction for preparing compounds of formula (I-a) can be performed in a reaction-inert solvent such as, for example, N,N-dimethylformamide, and in the presence of a suitable base such as, for example, sodium hydride, preferably at a temperature ranging between room temperature and reflux temperature.

The compounds of formula (I) wherein $R^1$ is $NR^4R^5$, represented by formula (I-c), can be prepared from either compounds of formula (VIII) or (IX) by suitable N-alkylation reactions as depicted herebelow, wherein W is as previously defined. These N-alkylations are conducted in a reaction-inert solvent such as, for example, an ether e.g. tetrahydofuran and preferably in the presence of a strong base, e.g. NaH.

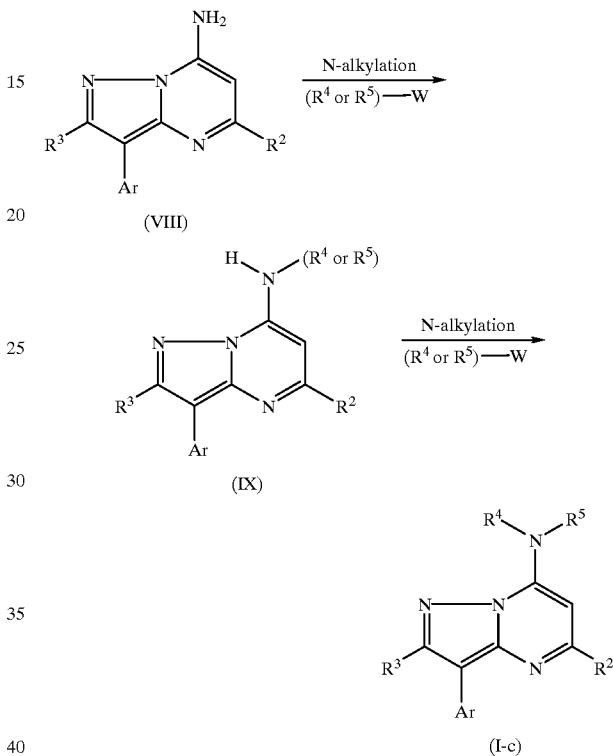

In certain instances, this reaction can give rise to side products wherein $R^2$ is alkylated by ($R^4$ or $R^5$)-W, in particular where $R^2$ is methyl and $R^4$ or $R^5$ is $C_{1-6}$alkyl.

As outlined below, compounds of formula (I) may be converted into each other following art-known transformation procedures.

The compounds of formula (I) wherein $R^3$ is $C_{1-6}$alkylthio can be converted into compounds of formula (I) wherein $R^3$ is $C_{1-6}$alkylsulfonyl or $C_{1-6}$alkylsulfoxy by an oxidation reaction, e.g. treatment with a peroxide such as 3-chloroperbenzoic acid in a reaction-inert solvent, e.g. dichloromethane. By controlling the amount of oxidant and other reaction parameters, either compounds of formula (I) wherein $R^3$ is $C_{1-6}$alkylsulfonyl or $C_{1-6}$alkylsulfoxy can be obtained, or a mixture of both, which subsequently can be separated by conventional methods, e.g. column chromatography.

The compounds of formula (I) may also be converted into each other via art-known reactions or functional group transformations. For instance, compounds of formula (I) bearing a hydroxy$C_{1-6}$alkyl group may be converted into compounds of formula (I) bearing a $C_{1-6}$alkylcarbonyloxy$C_{1-6}$alkyl group, e.g. by treatment with an acid anhydride in an reaction-inert solvent such as, e.g. dichloromethane, and optionally in the presence of a base such as, e.g. pyridine.

Compounds of formula (I) bearing a nitro group may be converted to compounds of formula (I) bearing an amino group and subsequently to compounds of formula (I) having a mono- or di($C_{1-6}$alkyl)amino group. Also, the amino group may be converted using a diazotization reaction to a halo.

Further, the Ar group of compounds of formula (I) can be halogenated using a halogenating agent such as, e.g. chlorine or bromine, in a suitable solvent, e.g. acetic acid, and optionally the reaction may be performed at a temperature ranging between room temperature and the reflux temperature of the reaction mixture.

Intermediates of formula (II) can be prepared according to the procedure as described in Robins et al., J. Heterocyclic Chem. 22:601–634, 1985.

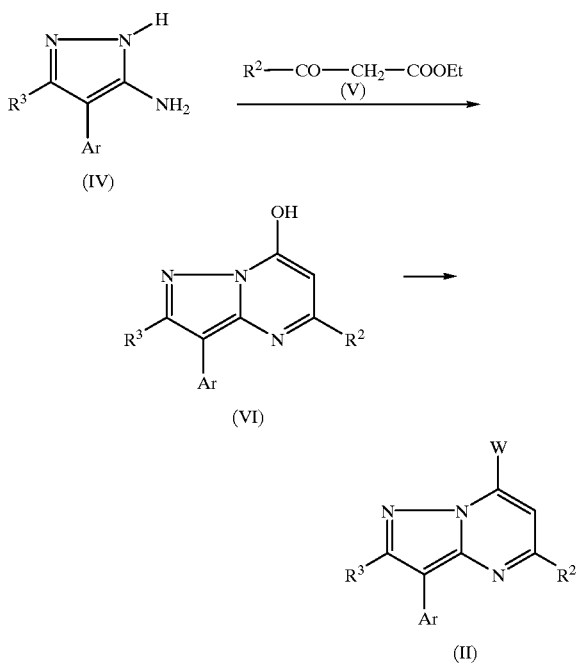

Aminopyrazole derivatives (IV) are reacted with a β-keto ester (V), preferably under reflux conditions and in a suitable reaction-inert solvent such as an ether, e.g. THF, yielding hydroxypyrazolopyrimidines (VI) which are converted into intermediates of formula (II) by converting the hydroxy group of intermediate (VI) into leaving group W, e.g. by treating (VI) with methanesulfonyloxy chloride or a halogenating reagent such as, e.g. $POCl_3$.

Intermediates of formula (VIII) are prepared by treating intermediates of formula (II) with ammonia.

In an embodiment, this invention also provides for intermediates of formula (II'), wherein W' represents hydroxy, halo, mesyloxy or tosyloxy; with the proviso that Ar is other than phenyl.

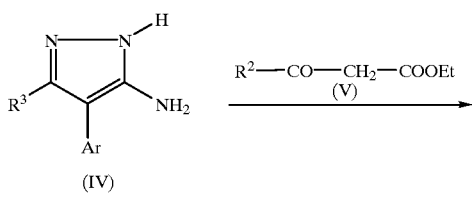

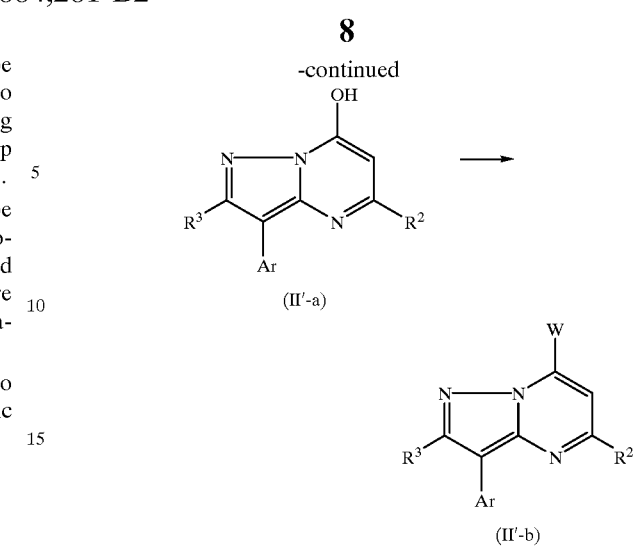

Said intermediates of formula (II') may be prepared according to procedures used to prepare intermediates of formula (II), thereby thereby yielding compounds of formula (II'-a), defined as compounds of formula (II') wherein W' is hydroxy; and optionally converting compounds of formula (II'-a) into compounds of formula (II'-b), defined as compounds of formula (II') wherein W' is other than hydroxy.

Stereoisomers may be prepared by separation of the end products of formula (I) following art-known procedures, e.g. by treatment with an optically active acid and separating the thus-formed diastereoisomeric salts by selective crystallization or column chromatography. Or, stereoisomers may be prepared by using stereoisomeric starting materials in any of the above reaction schemes or in the preparation of intermediates described hereinafter.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (J. Neuroscience 7:88, 1987) and Battaglia et al. (Synapse 1:572, 1987). As mentioned above, suitable CRF antagonists include compounds which demonstrate CRF receptor affinity. CRF receptor affinity may be determined by binding studies that measure the ability of a compound to inhibit the binding of a radiolabeled CRF (e.g. [$^{125}$I]tyrosine CFR) to receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, Biochem. Pharmacol. 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)). With reference to CRF receptor binding affinities, CRF receptor antagonists of this invention have a $K_i$ of less than 10 $\mu$M. In a preferred embodiment of this invention, a CRF receptor antagonist has a $K_i$ of less than 1 $\mu$M, and more preferably less than 0.25 $\mu$M (i.e., 250 nM).

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodiment of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (i.e., a compound of structure (I)) and a pharmaceutically acceptable carrier and/or diluent. The CRF receptor antagonist is present in the composition in an amount which is effective to treat a particular disorder, that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices, such as those disclosed in Remington's Pharmaceutical Sciences, Gennaro, Ed., Mack Publishing Co., Easton, USA, 1990.

In another embodiment, the present invention provides a method for treating a variety of disorders or illnesses, including endocrine, psychiatric and neurologic disorders or illnesses. Such methods include administering of a compound of the present invention to a warm-blooded animal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

Hence, this invention provides the use of compounds of formula (I) for the manufacture of a medicine for treating physiological conditions or disorders arising from the hypersecretion of corticotropin-releasing factor (CRF); and in a further embodiment the use of novel compounds of formula (I) as a medicine is provided.

The following examples are provided for purposes of illustration, not limition.

Experimental part

Hereinafter "THF" means tetrahydrofuran and "DCM" means dichloromethane.

A. Preparation of the intermediates

EXAMPLE A.1 a) 3-Amino-4-(2,4-dichlorophenyl)pyrazole and ethyl acetoacetate (2 equivalents) were dissolved in dioxane and heated under reflux overnight. The mixture was concentrated in vacuo and diluted with ethyl acetate. An off-white solid formed after 2 days standing was collected by vacuum filtration, yielding 3-(2,4-dichlorophenyl)-5-methyl-7-hydroxypyrazolo[2,3-a]pyrimidine (intermediate 1).

b) Intermediate 1 (300 mg) was mixed with $POCl_3$ (1.5 ml) and heated to reflux for 1 hour. The resultant purple solution was carefully transferred into ice-water. The product was extracted with ethyl acetate, washed with saturated sodium bicarbonate and brine, dried over MgSO$_4$ and concentrated in vacuo to give 3-(2,4-dichlorophenyl-5-methyl-7-chloropyrazolo[2,3-a]pyrinidine (intermediate 2) as a brown solid (260 mg, 82%).

EXAMPLE A.2 a) To a stirred solution of sodium hydride (60%, 25 mmol) in THF (10 ml) 6-(dimethylamino)-3-pyridineacetonitrile was added dropwise (10 mmol) in THF (10 ml). The solution was allowed to stir for 10 minutes before ethyl acetate (30 mmol) was added slowly. The resulting suspension was stirred at room temperature for another hour. The reaction mixture was concentrated under vacuum and dissolved in ethyl acetate/methanol (1:1) and filtered through silica. The filtrate was concentrated, yielding (intermediate 7).

b) A mixture of intermediate 7 and hydrazine hydrobromide (100 mmol) was dissolved in ethanol/water (9:1, total 100 ml) and refluxed for 1 hour. The reaction mixture was concentrated and the residue was partitioned between ethyl acetate and sodium bicarbonate solution. The combined extracts were dried over sodium sulfate, filtered and concentrated to dryness. The residue was dissolved in 1,4-dioxane (200 ml) and refluxed for 16 hours in the presence of ethyl acetoacetate. The reaction mixture was cooled an off-white solid precipitated out. Diethyl ether was added to aid in crystallation and the precipitate was filtered off and dried, yielding 3-[2-(dimethylamino)-5-pyridinyl]-2,5-dimethyl-7-hydroxypyrazolo[2,3-a]pyrimidine (intermediate 8).

c) Intermediate 8 was dissolved in POCl$_3$ (2 ml) and refluxed for 2 hours. The reaction mixture was cooled and poured onto ice. The solution was made basic (pH =9) by addition of solid sodium carbonate and extracted with diethyl ether. The combined organic layers were dried over sodium sulfate, filtered and concentrated, yielding 3-[6-(dimethylamino)-3-pyridinyl]-2,5-dimethyl-7-chloropyrazolo[2,3-a]pyrimidine (intermediate 9).

Table 1 lists the intermediates that were prepared according to one of the above Examples.

TABLE 1

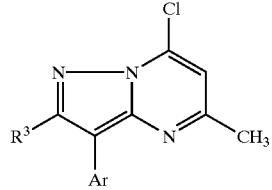

| Interm. No. | Ex. No. | R$^3$ | Ar |
|---|---|---|---|
| 2 | A.1 | H | 2,4-dichlorophenyl |
| 3 | A.1 | CH$_3$S | 2,4-dichlorophenyl |
| 4 | A.1 | CH$_3$ | 2,4-dichlorophenyl |
| 5 | A.1 | H | 4-chlorophenyl |
| 6 | A.1 | H | 2,6-dichlorophenyl |
| 13 | A.1 | CH$_3$ | 4-chlorophenyl |
| 14 | A.1 | CH$_3$ | 3-methoxyphenyl |
| 15 | A.1 | CH$_3$ | 4-methoxyphenyl |
| 16 | A.1 | CH$_3$ | 2,4-dimethoxyphenyl |
| 17 | A.1 | CH$_3$CH$_2$ | 3,4-dimethoxyphenyl |
| 18 | A.1 | H | 2,4,6-trimethoxyphenyl |
| 9 | A.2 | CH$_3$ | 6-dimethylamino-3-pyridinyl |
| 10 | A.2 | CH$_3$ | 6-dimethylamino-4-methyl-3-pyridinyl |

TABLE 1-continued

| Interm. No. | Ex. No. | R$^3$ | Ar |
|---|---|---|---|
| 11 | A.2 | CH$_3$ | 6-methyl-5-nitro-2-pyridinyl |
| 12 | A.2 | CH$_3$ | 5-chloro-2-pyridinyl |
| 19 | A.1 | CH$_3$ | 6-methyl-3-pyridinyl |
| 20 | A.1 | CH$_3$ | 3-methyl-5-nitro-2-pyridinyl |

B. Preparation of the final products

EXAMPLE B.1

A mixture of intermediate 2 (21 mg) and N-propyl-N-cyclopropanemethylamine (75 mg) was heated in a sealed reaction vial at 100° C. overnight. Chromatography on a preparative TLC plate with 1:5 ethyl acetate-hexanes gave 3-(2,4-dichlorophenyl)-5-methyl-7-(N-propyl-N-cyclopropanemethylamino)-pyrazolo[2,3-a]pyrimidine (compound 17) (17.4 mg) and 3-(2,4-dichlorophenyl)-5-methyl-7-(N-cyclopropanemethylamino)-pyrazolo[2,3-a]pyrimidine (compound 8) (1 mg).

In a similar way, starting from intermediate 2 and (S)-(-)-leucinol respectively (R)-(+)-leucinol, (S)-2[[3-(2,4-dichlorophenyl)-5-methyl-7-pyrazolo[2,3-a]pyrimidinyl]amino]-4-methyl-1-pentanol (compound 11) and its R-analog (compound 12) were prepared.

EXAMPLE B.2

A solution of intermediate 10 (8 g) and di-n-propylamine (13 g) in acetonitrile (50 ml) was heated at reflux for 3 hours. The mixture was filtrated through a short silica gel plug with ethyl acetate and the filtrate was concentrated in vacuo to provide a light yellow solid which was recrystallized from ether-hexanes, yielding 8.9 g (93%) of 3-[6-(dimethylamno)-4-methyl-3-pyridinyl]-2,5-dimethyl-N,N-dipropylpyrazolo[2,3-a]-pyrimidin-7-amine (compound 53).

Compound 53 was also converted to its hydrochloric acid addition salt by dissolving compound 53 (8.1 g) in a mixture of diethyl ether (150 ml) and DCM (50 ml) and treating said mixture with HCl in diethyl ether (1M, 21.3 ml) dropwise with stirring. The resulting off-white solid was collected by filtration, yielding 8.7 g (98%) of 3-[6-(dimethylamino)-4-methyl-3-pyridinyl]-2,5-dimethyl-N,N-dipropyl-pyrazolo[2,3-a]pyrimidin-7-amine monohydrochloride.

EXAMPLE B.3

Intermediate 3 (15 mg) was dissolved in ethanol (0.5 ml) and stirred in the presence of sodium ethoxide (12 mg) for 1 hour. Chromatography on silica gel gave 3-(2,4-dichlorophenyl)-7-(ethoxy)-5-methyl-2-methylthio-pyrazolo[2,3-a]pyrimidine (compound 50).

EXAMPLE B.4

A solution of compound 6 (14 mg) in THF (3 ml) was treated with sodium hydride (60 mg, excess) at room temperature for 5 minutes, followed by Iodopropane (0.3 ml).

The reaction was stirred at room temperature overnight and quenched with methanol (0.5 ml). The resultant mixture was loaded onto a preparative TLC plate and developed with 1:5 ethyl acetate-hexanes to give 3-(2,4-dichlorophenyl)-5-methyl-7-[N-(3-methoxypropyl)-N-propylamino]-pyrazolo[2,3-a]pyrimidine (compound 45) (5.7 mg) as a colorless oil, 3-(2,4-dichlorophenyl)-5-butyl-7-[N-(3-methoxypropyl)-N-propylamino]-pyrazolo[2,3-a]pyrimidine (compound 46) (4 mg) and 3-(2,4-dichlorophenyl)-5-butyl-7-[3-methoxypropylamino]-pyrazolo[2,3-a]pyrimidine (compound 47) (3.5 mg).

EXAMPLE B.5

Compound 26 (8 mg) was dissolved in DCM (1 ml) and treated with acetic anhydride (0.1 ml) and pyridine (0.1 ml). The mixture was stirred at room temperature overnight and concentrated in vacuo. The residue was diluted with ethyl acetate and filtrated through a short silica gel column. Concentration of the filtrate gave 3-(2,4-dichlorophenyl)-5-methyl-7-[N-(2-acetoxyethyl)-N-benzylamino]-pyrazolo[2,3-a]-pyrimidine (compound 27) (8.6 mg) as a colorless oil.

EXAMPLE B.6

A solution of compound 40 (20 mg) in DCM (3 ml) was treated with 3-chloroperbenzoic acid (19 mg). The solution was stirred at room temperature for 1 hour. Chromatography on a silica gel plate with ethyl acetate-hexanes (1:1) yielded compound 43 and compound 44.

EXAMPLE B.7

A mixture of compound 55, palladium on activated carbon (100 mg) in dry ethanol (100 ml) was put on the hydrogenation unit and hydrogenation was carried out at 2.7 10$^5$ Pa (40 psi) for 2 hours. The reaction mixture was filtered and concentrated. The residue was dissolved in diethyl ether and concentrated, yielding 1.49 g of 3-(5-amino-3-methyl-2-pyridinyl)-2,5-dimethyl-N,N-dipropyl-pyrazolo[2,3-a]pyrimidine-7-amine (compound 56).

EXAMPLE B.8

To a stirring solution of compound 56 (1.39 g) and aqueous formaldehyde (6.4 g) in ACN (20 ml) was added sodium cyanoborohydride (743 mg) at 0° C. Glacial acetic acid (1 ml) was added and the reaction mixture was stirred at room temperature for 2 hours. The reaction mixture was partitioned between ethyl acetate and saturated aqueous sodium bicarbonate. The organic layer was washed with brine, dried over sodium sulfate, filtered, concentrated to dryness and purified by flash column chromatography on silica gel ($CH_2Cl_2$/$CH_3OH$/$NH_4OH$ 150:10: 1). The desired fraction was isolated, yielding 1.30 g of 3-[5-(dimethylamino)-3-methyl-2-pyridinyl]-2,5-dimethyl-N,N-dipropyl-pyrazolo[2,3-a]pyrimidine-7-amine (compound 57).

EXAMPLE B.9

To a solution of compound 56 (100 mg) in a mixture of concentrated HCl (1 ml) and water (1 ml), cooled in an ice bath, was added a solution of sodium nitrite (21 mg) in water (1 ml). The solution was added to a mixture of copper(I) chloride (281 mg) in concentrated HCl with stirring in an ice bath. A solid separated and the mixture was heated to 60° C. and a clear solution was obtained. The reaction mixture was basified with NaOH, extracted with ethyl acetate, washed with brine and concentrated. Purification by preparative TLC yielded 16 mg of compound 98.

EXAMPLE B.10

Compound 56 (100 mg) was added to a solution of fluoroboric acid (48% wt in water, 2 ml), cooled in an ice bath, followed by addition of a solution of sodium nitrite (20 mg) in water (1 ml). The temperature was kept under 10° C. The solid was collected by filtration, dried and partitioned between an aqueous sodium bicarbonate solution and ethyl acetate. The organic layer was washed with brine, concentrated and the residue was purified by preparative TLC yielding 20 mg of compound 100.

Tables 2 to 5 list the compounds that were prepared according to one of the above Examples and tables 6 and 7 list the analytical data for these compounds.

TABLE 2

| Co. No. | Ex. No. | R$^4$ | R$^5$ | Ar |
|---|---|---|---|---|
| 1 | B.1 | hydrogen | n-propyl | 2,4-dichlorophenyl |
| 2 | B.1 | hydrogen | 2-methylpropyl | 2,4-dichlorophenyl |
| 3 | B.1 | hydrogen | 1,1-dimethylethyl | 2,4-dichlorophenyl |
| 4 | B.1 | hydrogen | 3-hydroxypropyl | 2,4-dichlorophenyl |
| 5 | B.1 | hydrogen | 3-pentyl | 2,4-dichlorophenyl |
| 6 | B.1 | hydrogen | $CH_3O(CH_2)_3$— | 2,4-dichlorophenyl |
| 7 | B.1 | hydrogen | $(CH_3)_2CHO(CH_2)_3$— | 2,4-dichlorophenyl |
| 8 | B.1 | hydrogen | cyclopropylmethyl | 2,4-dichlorophenyl |
| 9 | B.1 | hydrogen | 3-methyl-2-butyl | 2,4-dichlorophenyl |
| 10 | B.1 | hydrogen | 4-methyl-2-pentyl | 2,4-dichlorophenyl |

TABLE 2-continued

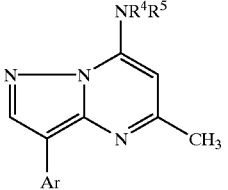

| Co. No. | Ex. No. | R⁴ | R⁵ | Ar |
|---|---|---|---|---|
| 11 | B.1 | hydrogen | 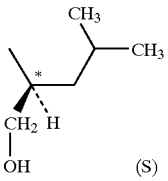 (S) | 2,4-dichlorophenyl |
| 12 | B.1 | hydrogen | 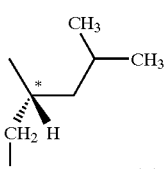 (R) | 2,4-dichlorophenyl |
| 13 | B.1 | hydrogen | 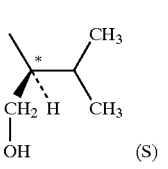 (S) | 2,4-dichlorophenyl |
| 14 | B.3 | methyl | cyclopropylmethyl | 2,4-dichlorophenyl |
| 15 | B.1 | ethyl | n-butyl | 2,4-dichlorophenyl |
| 16 | B.2 | n-propyl | n-propyl | 2,4-dichlorophenyl |
| 17 | B.1 | n-propyl | cyclopropylmethyl | 2,4-dichlorophenyl |
| 18 | B.1 | n-propyl | HOCH$_2$CH$_2$— | 2,4-dichlorophenyl |
| 19 | B.1 | n-propyl | CH$_3$O(CH$_2$)$_2$— | 2,4-dichlorophenyl |
| 20 | B.2 | n-propyl | n-propyl | 4-chlorophenyl |
| 21 | B.1 | n-propyl | cyclopropyl | 2,6-dichlorophenyl |
| 22 | B.1 | n-propyl | CH$_3$O(CH$_2$)$_2$ | 2,6-dichlorophenyl |
| 23 | B.4 | n-butyl | cyclopropylmethyl | 2,4-dichlorophenyl |
| 24 | B.1 | 2-methylpropyl | cyclopropylmethyl | 2,4-dichlorophenyl |
| 25 | B.1 | 3-methyl-2-butyl | cyclopropylmethyl | 2,4-dichlorophenyl |
| 26 | B.1 | HOCH$_2$CH$_2$— | phenylmethyl | 2,4-dichlorophenyl |
| 27 | B.5 | CH$_3$COO(CH$_2$)$_2$— | phenylmethyl | 2,4-dichlorophenyl |
| 28 | B.5 | CH$_3$COO(CH$_2$)$_2$— | n-propyl | 2,4-dichlorophenyl |
| 29 | B.4 | allyl | cyclopropylmethyl | 2,4-dichlorophenyl |
| 45 | B.4 | n-propyl | CH$_3$O(CH$_2$)$_3$ | 2,4-dichlorophenyl |
| 58 | B.1 | CH$_3$O(CH$_2$)$_2$— | CH$_3$O(CH$_2$)$_2$— | 2,4-dichlorophenyl |
| 59 | B.1 | hydrogen | CH$_3$OCH$_2$CH(CH$_3$)— | 2,4-dichlorophenyl |
| 60 | B.1 | hydrogen | 1-hydroxy-2-hexyl | 2,4-dichlorophenyl |
| 61 | B.1 | hydrogen | 1-hydroxy-2-pentyl | 2,4-dichlorophenyl |
| 62 | B.2 | n-propyl | n-propyl | 6-dimethylamino-2,4-dimethyl-3-pyridinyl |
| 63 | B.1 | ethyl | n-butyl | 6-dimethylamino-2,4-dimethyl-3-pyridinyl |
| 64 | B.1 | n-propyl | cyclopropylmethyl | 6-dimethylamino-2,4-dimethyl-3-pyridinyl |
| 65 | B.1 | n-propyl | cyclopropylmethyl | 6-methyl-3-pyridinyl |
| 66 | B.1 | n-butyl | n-butyl | 6-methyl-3-pyridinyl |
| 67 | B.1 | n-propyl | cyclopropylmethyl | 2,4-dimethoxyphenyl |
| 68 | B.2 | n-propyl | n-propyl | 2,4,6-trimethoxyphenyl |
| 69 | B.1 | n-propyl | CH$_3$O(CH$_2$)$_2$— | 2,4,6-trimethoxyphenyl |
| 70 | B.1 | n-propyl | cyclopropylmethyl | 2,4,6-trimethoxyphenyl |
| 71 | B.1 | ethyl | n-butyl | 2,4,6-trimethoxyphenyl |
| 72 | B.1 | ethyl | ethyl | 2,4,6-trimethoxyphenyl |

TABLE 3

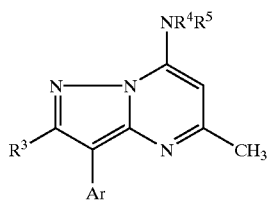

| Co. No. | Ex. No. | R³ | R⁴ | R⁵ | Ar |
|---|---|---|---|---|---|
| 30 | B.1 | CH₃S | hydrogen | n-propyl | 2,4-dichlorophenyl |
| 31 | B.1 | CH₃S | hydrogen | 2-propyl | 2,4-dichlorophenyl |
| 32 | B.1 | CH₃S | hydrogen | 3-heptyl | 2,4-dichlorophenyl |
| 34 | B.1 | CH₃S | hydrogen | 2-methoxyphenylmethyl | 2,4-dichlorophenyl |
| 35 | B.1 | CH₃S | methyl | methyl | 2,4-dichlorophenyl |
| 36 | B.1 | CH₃S | ethyl | ethyl | 2,4-dichlorophenyl |
| 37 | B.2 | CH₃S | n-propyl | n-propyl | 2,4-dichlorophenyl |
| 38 | B.1 | CH₃S | n-propyl | cyclopropylmethyl | 2,4-dichlorophenyl |
| 39 | B.1 | CH₃S | 2-propyl | 2-propyl | 2,4-dichlorophenyl |
| 40 | B.1 | CH₃S | n-butyl | n-butyl | 2,4-dichlorophenyl |
| 41 | B.1 | CH₃S | n-butyl | cyclopropylmethyl | 2,4-dichlorophenyl |
| 42 | B.1 | CH₃S | allyl | allyl | 2,4-dichlorophenyl |
| 43 | B.6 | CH₃SO | n-propyl | cyclopropylmethyl | 2,4-dichlorophenyl |
| 44 | B.6 | CH₃SO₂ | n-propyl | cyclopropylmethyl | 2,4-dichlorophenyl |
| 73 | B.2 | CH₃CH₂ | n-propyl | n-propyl | 3,4-dimethoxyphenyl |

TABLE 4

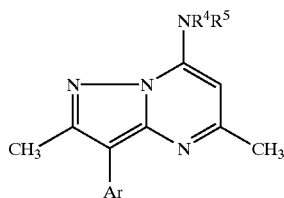

| Co. No. | Ex. No. | R⁴ | R⁵ | Ar |
|---|---|---|---|---|
| 48 | B.2 | n-propyl | n-propyl | 4-chlorophenyl |
| 49 | B.1 | n-propyl | cyclopropylmethyl | 2,4-dichlorophenyl |
| 51 | B.1 | n-propyl | CH₃O(CH₂)₂— | 2,4-dimethoxyphenyl |
| 52 | B.2 | n-propyl | n-propyl | 6-dimethylamino-3-pyridinyl |
| 53 | B.2 | n-propyl | n-propyl | 6-dimethylamino-4-methyl-3-pyridinyl |
| 54 | B.2 | n-propyl | n-propyl | 5-chloro-2-pyridinyl |
| 55 | B.2 | n-propyl | n-propyl | 3-methyl-5-nitro-2-pyridinyl |
| 56 | B.7 | n-propyl | n-propyl | 5-amino-3-methyl-2-pyridinyl |
| 57 | B.8 | n-propyl | n-propyl | 5-dimethylamino-3-methyl-2-pyridinyl |
| 74 | B.1 | CH₃O(CH₂)₂— | CH₃O(CH₂)₂— | 4-chlorophenyl |
| 75 | B.1 | HOCH₂CH₂— | phenylmethyl | 4-chlorophenyl |
| 76 | B.1 | hydrogen | 1-hydroxy-2-hexyl | 4-chlorophenyl |
| 77 | B.1 | hydrogen | 1-hydroxy-2-pentyl | 4-chlorophenyl |
| 78 | B.1 | hydrogen | CH₃S(CH₂)₂— | 4-chlorophenyl |
| 79 | B.1 | hydrogen | ![structure with CH₃, CH₃, CH₂, H, OH (S)] | 4-chlorophenyl |
| 80 | B.1 | hydrogen | 1-hydroxy-2-hexyl | 6-dimethylamino-4-methyl-3-pyridinyl |
| 81 | B.1 | ethyl | n-butyl | 6-dimethylamino-4-methyl-3-pyridinyl |
| 82 | B.1 | n-propyl | cyclopropylmethyl | 6-dimethylamino-4-methyl- |

TABLE 4-continued

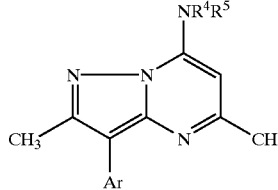

| | | | | |
|---|---|---|---|---|
| 83 | B.1 | n-propyl | phenylmethyl | 3-pyridinyl |
| | | | | 6-dimethylamino-4-methyl-3-pyridinyl |
| 84 | B.1 | allyl | allyl | 6-dimethylamino-4-methyl-3-pyridinyl |
| 85 | B.1 | n-butyl | n-butyl | 6-dimethylamino-4-methyl-3-pyridinyl |
| 86 | B.1 | hydrogen | 3-pentyl | 6-dimethylamino-4-methyl-3-pyridinyl |
| 87 | B.1 | hydrogen | 2-propyl | 6-dimethylamino-4-methyl-3-pyridinyl |
| 88 | B.1 | hydrogen | 4-methyl-2-pentyl | 6-dimethylamino-4-methyl-3-pyridinyl |
| 89 | B.1 | methyl | n-butyl | 6-dimethylamino-4-methyl-3-pyridinyl |
| 90 | B.2 | n-propyl | n-propyl | 6-dimethylamino-2-methyl-3-pyridinyl |
| 91 | B.1 | n-propyl | cyclopropylmethyl | 6-dimethylamino-2-methyl-3-pyridinyl |
| 92 | B.1 | ethyl | n-butyl | 6-dimethylamino-2-methyl-3-pyridinyl |
| 93 | B.1 | n-butyl | n-butyl | 6-dimethylamino-2-methyl-3-pyridinyl |
| 94 | B.1 | n-propyl | n-propyl | 4,6-dimethyl-3-pyridinyl |
| 95 | B.1 | n-propyl | cyclopropylmethyl | 4,6-dimethyl-3-pyridinyl |
| 96 | B.2 | n-propyl | n-propyl | 6-dimethylamino-2,4-dimethyl-3-pyridinyl |
| 97 | B.1 | n-propyl | cyclopropylmethyl | 6-dimethylamino-2,4-dimethyl-3-pyridinyl |
| 98 | B.9 | n-propyl | n-propyl | 5-chloro-3-methyl-2-pyridinyl |
| 99 | B.9 | n-propyl | n-propyl | 5-iodo-3-methyl-2-pyridinyl |
| 100 | B.10 | n-propyl | n-propyl | 5-fluoro-3-methyl-2-pyridinyl |
| 101 | B.2 | n-propyl | n-propyl | 3-chloro-5-trifluoromethyl-2-pyridinyl |
| 102 | B.1 | CH$_3$O(CH$_2$)$_2$— | CH$_3$O(CH$_2$)$_2$— | 3-chloro-5-trifluoromethyl-2-pyridinyl |
| 103 | B.2 | n-propyl | n-propyl | 3,5-dichloro-2-pyridinyl |
| 104 | B.1 | n-propyl | CH$_3$O(CH$_2$)$_2$— | 3,5-dichloro-2-pyridinyl |
| 105 | B.1 | n-propyl | cyclopropylmethyl | 3,5-dichloro-2-pyridinyl |
| 106 | B.2 | n-propyl | n-propyl | 3-methyl-5-methoxy-2-pyridinyl |
| 107 | B.8 | n-propyl | n-propyl | 5-diethylamino-3-methyl-2-pyridinyl |
| 33 | B.8 | n-propyl | n-propyl | 6-diethylamino-4-methyl-3-pyridinyl |
| 108 | B.8 | n-propyl | n-propyl | 5-N-piperidinyl-3-methyl-2-pyridinyl |
| 109 | B.2 | n-propyl | n-propyl | 5-methyl-3-nitro-2-pyridinyl |
| 110 | B.2 | n-propyl | n-propyl | 3-amino-5-methyl-2-pyridinyl |
| 111 | B.9 | n-propyl | n-propyl | 3-chloro-5-methyl-2-pyridinyl |
| 112 | B.2 | n-propyl | n-propyl | 3-methylamino-5-methyl-2-pyridinyl |
| 113 | B.2 | n-propyl | n-propyl | 3-dimethylamino-5-methyl-2-pyridinyl |
| 114 | B.2 | n-propyl | n-propyl | 2-methyl-5-pyridinyl |
| 115 | B.1 | n-propyl | cyclopropylmethyl | 4-isopropylphenyl |
| 116 | B.2 | n-propyl | n-propyl | 3,4-dimethoxyphenyl |
| 117 | B.1 | n-propyl | CH$_3$O(CH$_2$)$_2$— | 3,4-dimethoxyphenyl |
| 118 | B.1 | n-propyl | cyclopropyl | 2,4-dimethoxyphenyl |
| 119 | B.1 | hydrogen | CH$_3$O(CH$_2$)$_2$— | 2,4-dimethoxyphenyl |
| 120 | B.1 | n-propyl | HO(CH$_2$)$_2$— | 2,4-dimethoxyphenyl |
| 121 | B.8 | n-propyl | n-propyl | 5-methylamino-3-methyl-2-pyridinyl |
| 122 | B.2 | n-propyl | n-propyl | 2,4-dimethoxyphenyl |
| 123 | B.1 | ethyl | n-butyl | 2,4-dimethoxyphenyl |
| 124 | B.1 | n-propyl | 2-hydroxypropyl | 2,4-dimethoxyphenyl |
| 125 | B.2 | n-propyl | n-propyl | 4-methoxyphenyl |
| 126 | B.2 | n-propyl | n-propyl | 3-methoxyphenyl |
| 127 | B.1 | n-propyl | cyclopropylmethyl | 3-methoxyphenyl |

TABLE 4-continued
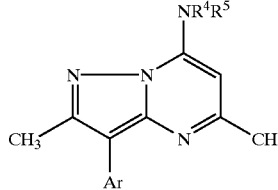
| Co. No. | Ex. No. | R⁴ and R⁵ taken together | Ar |
|---|---|---|---|
| 128 | B.1 | 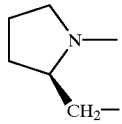 | 4-chlorophenyl |
| 129 | B.1 | 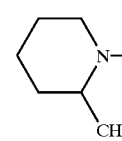 | 4-chlorophenyl |
| 130 | B.1 | 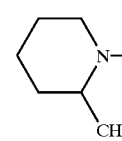 | 6-dimethylamino-4-methyl-3-pyridinyl |
| 131 | B.1 | 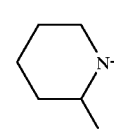 | 6-dimethylamino-4-methyl-3-pyridinyl |
TABLE 5
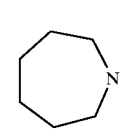
| Co. No. | Ex. No. | R¹ | R² | R³ | Ar |
|---|---|---|---|---|---|
| 46 | B.4 | 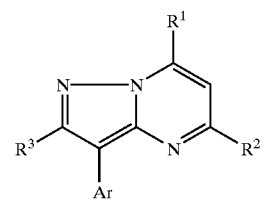 | n-C₄H₉ | H | 2,4-dichlorophenyl |
| 47 | B.4 | 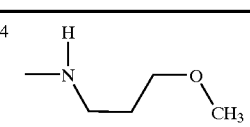 | n-C₄H₉ | H | 2,4-dichlorophenyl |
| 50 | B.3 | CH₃CH₂O— | CH₃ | CH₃—S— | 2,4-dichlorophenyl |

TABLE 6

Analytical data

| Co. No. | ¹H NMR data (CDCl₃) | MS M+1 |
|---|---|---|
| 1 | δ0.45(m, 2H), 0.78(m, 2H), 1.20(m, 1H), 2.84(s, 3H), 3.40(d, 2H), 5.98(s, 1H), 7.41(dd, 1H), 7.52(d, 1H), 7.76(d, 1H), 8.32(s, 1H) | 335 |
| 2 | δ0.88(d, 3H), 1.05(d, 3H), 1.74(m, 1H), 2.52(s, 3H), 3.20(t, 2H), 5.87(s, 1H), 6.40(t, 1H), 7.30(dd, 1H), 7.47(d, 1H), 7.99(d, 1H), 8.42(s, 1H) | 349 |
| 3 | δ1.57(s, 9H), 2.54(s, 3H), 6.05(s, 1H), 6.48(s, 1H), 7.31(d, 1H), 7.47(s, 1H), 7.99(d, 1H), 8.39(s, 1H) | 349 |
| 4 | δ1.97(m, 2H), 2.43(s, 3H), 3.62(m, 2H), 3.75(t, 3H), 4.00(brs, 1H), 6.18(s, 1H), 7.39(dd, 1H), 7.52(d, 1H), 8.19(s, 1H), 8.43(s, 1H) | 351 |
| 5 | δ1.03(t, 6H), 1.60–1.85(m, 4H), 2.56(s, 3H), 3.49(m, 1H), 5.92(s, 1H), 6.19(d, 1H), 7.35(dd, 1H), 7.50(dd, 1H), 8.01(d, 1H), 8.44(s, 1H) | 363 |
| 6 | δ2.02(m, 2H), 2.51(s, 3H), 3.40(s, 3H), 3.51(m, 4H), 5.91(s, 1H), 6.71(t, 1H), 7.31(dd, 1H), 7.47(d, 1H), 7.99(d, 1H), 8.42(s, 1H) | 365 |
| 7 | δ1.23(d, 6H), 2.00(m, 2H), 2.52(s, 3H), 3.51(dd, 2H), 3.59(m, 2H), 5.90(s, 1H), 6.92(t, 1H), 7.31(dd, 1H), 7.46(d, 1H), 8.00(d, 1H), 8.41(s, 1H) | 393 |
| 8 | δ0.35(m, 2H), 0.68(m, 2H), 1.25(m, 1H), 2.52(s, 3H), 3.23(dd, 2H), 5.88(s, 1H), 6.40(t, 1H), 7.32(d, 1H), 7.48(s, 1H), 7.99(s, 1H), 8.43(s, 1H) | 347 |
| 9 | δ1.03(d, 3H), 1.06(d, 3H), 1.31(d, 3H), 1.95(m, 1H), 2.52(s, 3H), 3.54(m, 1H), 5.88(s, 1H), 6.23(d, 1H), 7.32(d, 1H), 7.47(s, 1H), 7.98(d, 1H), 8.41(s, 1H) | 363 |
| 10 | δ0.95(d, 3H), 0.97(d, 3H), 1.40–1.80(m, 3H), 2.53(s, 3H), 3.76(m, 1H), 5.89(s, 1H), 6.12(d, 1H), 7.32(d, 1H), 7.47(s, 1H), 7.97(d, 1H), 8.40(s, 1H) | 377 |
| 11 | δ0.94(d, 3H), 0.99(d, 3H), 1.53(m, 1H), 1.76(m, 1H), 2.50(s, 3H), 2.93(brs, 1H), 3.48(m, 1H), 3.76(m, 1H), 5.97(s, 1H), 6.22(d, 1H), 7.35(dd, 1H), 7.51(d, 1H), 7.95(d, 1H), 8.36(s, | 393 |
| 12 | δ0.92(d, 3H), 0.97(d, 3H), 1.52(m, 2H), 1.72(m, 1H), 2.47(s, 3H), 3.02(brs, 1H), 3.42(m, 1H), 3.72(m, 2H), 5.94(s, 1H), 6.20(d, 1H), 7.33(d, 1H), 7.49(s, 1H), 7.92(d, 1H), 8.33(s, | 393 |
| 13 | δ0.99(d, 6H), 1.98(m, 1H), 2.44(s, 3H), 3.22(brs, 1H), 3.46(m, 2H), 3.73(m, 1H), 5.88(s, 1H), 6.31(d, 1H), 7.32(d, 1H), 7.48(s, 1H), 7.92(d, 1H), 8.32(s, 1H) | 379 |
| 14 | δ0.21(m, 2H), 0.54(m, 2H), 1.10(m, 1H), 2.53(s, 3H), 3.28(s, 3H), 3.91(d, 2H), 5.99(s, 1H), 7.32(d, 1H), 7.48(s, 1H), 7.97(d, 1H), 8.43(s, 1H) | 379 |
| 15 | δ0.96(t, 3H), 1.31(t, 3H), 1.38(m, 2H), 1.71(m, 2H), 2.49(s, 3H), 3.74(t, 2H), 3.65(q, 2H), 5.90(s, 1H), 7.30(dd, 1H), 7.46(d, 1H), 7.97(d, 1H), 8.40(s, 1H) | 377 |
| 16 | δ0.96(t, 6H), 1.73(m, 4H), 2.49(s, 3H), 3.73(t, 4H), 5.88(s, 1H), 7.33(dd, 1H), 7.46(d, 1H), 7.98(d, 1H), 8.40(s, 1H) | 377 |
| 17 | δ0.26(m, 2H), 0.58(m, 2H), 0.98(t, 3H), 1.18(m, 1H), 1.76(m, 2H), 2.53(s, 3H), 3.76(d, 2H), 3.81(t, 2H), 6.02(s, 1H), 7.34(dd, 1H), 7.49(dd, 1H), 8.44(s, 1H) | 389 |
| 18 | δ1.04(t, 3H), 1.77(m, 2H), 2.53(s, 3H), 3.47(t, 2H), 3.98(m, 2H), 4.06(m, 2H), 5.52(brs, 1H), 6.03(s, 1H), 7.33(d, 1H), 7.48(s, 1H), 7.93(d, 1H), 8.39(s, 1H) | 379 |
| 19 | δ0.98(t, 3H), 1.76(m, 2H), 2.50(s, 3H), 3.35(s, 3H), 3.67(t, 2H), 3.72(m, 2H), 4.14(brs, 3H), 5.95(s, 1H), 7.29(d, 1H), 7.47(s, 1H), 7.97(d, 1H), 8.39(s, 1H) | 393 |
| 20 | δ0.96(t, 6H), 1.73(m, 4H), 2.55(s, 3H), 3.74(t, 4H), 5.90(s, 1H), 7.40(d, 2H), 8.04(d, 2H), 8.25(s, 1H) | 343 |
| 21 | δ0.26(m, 2H), 0.51(m, 2H), 0.92(t, 3H), 1.10(m, 1H), 1.69(m, 2H), 2.72(s, 3H), 3.41(d, 2H), 3.47(t, 2H), 6.17(s, 1H), 7.18(t, 1H), 7.43(d, 2H), 7.99(s, 1H) | 389 |
| 22 | δ0.93(t, 3H), 1.67(m, 2H), 2.71(s, 3H), 3.32(s, 3H), 3.44(t, 2H), 3.61(m, 2H), 3.68(m, 2H), 6.16(s, 1H), 7.17(t, 1H), 7.41(d, 2H), 7.99(s, 1H) | 393 |
| 23 | δ0.24(m, 2H), 0.55(m, 2H), 0.95(t, 3H), 1.38(m, 2H), 1.69(m, 2H), 2.51(s, 3H), 3.74(d, 2H), 3.82(t, 2H), 6.00(s, 1H), 7.31(dd, 1H), 7.48(dd, 1H), 7.98(d, 1H), 8.42(s, 1H) | 403 |
| 24 | δ0.28(m, 2H), 0.50(m, 2H), 0.94(d, 6H), 1.10(m, 1H), 2.05(m, 1H), 2.52(s, 3H), 3.62(d, 2H), 3.82(d, 2H), 6.03(s, 1H), 7.32(d, 1H), 7.47(s, 1H), 7.99(d, 1H), 8.43(s, 1H) | 403 |
| 25 | δ0.17(m, 2H), 0.47(m, 2H), 0.97(t, 6H), 1.05(m, 1H), 1.67(m, 4H), 2.52(s, 3H), 2.43(d, 2H), 4.71(m, 1H), 6.13(s, 1H), 7.32(dd, 1H), 7.47(d, 1H), 8.02(d, 1H), 8.43(s, 1H) | 417 |
| 26 | δ2.41(s, 3H), 4.01(m, 2H), 4.15(m, 2H), 4.79(s, 2H), 5.62(brs, 1H), 6.02(s, 1H), 7.35(m, 6H), 7.48(s, 1H), 7.91(d, 1H), 8.41(s, 1H) | 427 |
| 27 | δ1.91(s, 3H), 2.47(s, 3H), 4.20(t, 2H), 4.43(t, 2H), 4.96(s, 2H), 6.03(s, 1H), 7.34(m, 6H), 7.49(s, 1H), 7.94(d, 1H), 8.44(s, 1H) | 469 |
| 28 | δ0.98(t, 3H), 1.74(m, 2H), 1.93(s, 3H), 2.49(s, 3H), 3.59(m, 2H), 4.84(m, 2H), 4.39(m, 2H), 5.95(s, 1H), 7.30(dd, 1H), 7.46(d, 1H), 7.92(d, 1H), 8.38(s, 1H) | 421 |
| 29 | δ0.28(m, 2H), 0.60(m, 2H), 1.20(m, 1H), 2.51(s, 3H), 3.70(d, 2H), 4.50(d, 2H), 5.29(d, 1H), 5.30(d, 1H), 5.96(m, 1H), .6.05(s, 1H), 7.32(dd, 1H), 7.48(d, 1H), 7.96(d, 1H), 8.44(s, 1H) | 387 |
| 30 | δ1.07(t, 3H), 1.80(m, 2H), 2.46(s, 3H), 2.55(s, 3H), 3.36(dt, 2H), 5.82(s, 1H), 6.29(t, 1H), 7.29(d, 1H), 7.38(d, 1H), 7.51(s, 1H) | 381 |
| 31 | δ1.41(d, 6H), 2.46(s, 3H), 2.55(s, 3H), 3.85(m, 1H), 5.82(s, 1H), 6.08(d, 1H), 7.29(d, 1H), 7.39(d, 1H), 7.51(s, 1H) | 381 |
| 32 | δ0.92(t, 3H), 1.01(t, 3H), 1.25–1.80(m, 8H), 2.45(s, 3H), 2.54(s, 3H), 3.48(m, 1H), 5.79(s, 1H), 6.02(d, 1H), 7.27(d, 1H), 7.39(d, 1H), 7.50(s, 1H) | 437 |
| 33 | δ0.96(t, 3H), 1.06(t, 3H), 1.74(m, 2H), 2.15(s, 3H), 2.34(s, 3H), 2.41(s, 3H), 3.56(t, 4H), 3.79(t, 4H), 5.77(s, 1H), 6.41(t, 1H), 7.54(s, 1H) | — |
| 34 | δ2.45(s, 3H), 2.56(s, 3H), 3.93(s, 3H), 4.60(d, 2H), 5.90(s, 1H), 6.70(t, 1H), 6.99(t, 2H), 7.27–7.41(m, 4H), 7.52(s, 1H) | 459 |
| 35 | δ2.44(s, 3H), 2.60(s, 3H), 3.35(s, 6H), 5.00(brs, 1H), 5.84(s, 1H), 7.29(d, 1H), 7.38(d, 1H), 7.51(s, 1H) | 367 |
| 36 | δ1.36(s, 6H), 2.42(s, 3H), 2.59(s, 3H), 3.80(m, 4H), 5.80(s, 1H), 7.29(d, 1H), 7.38(d, 1H), 7.51(s, 1H) | 395 |
| 37 | δ0.98(t, 6H), 1.78(m, 4H), 2.40(s, 3H), 2.59(s, 3H), 3.69(m, 4H), 5.74(s, 1H), 7.28(d, 1H), 7.48(d, 1H) | 423 |
| 38 | δ0.30(m, 2H), 0.62(m, 2H), 0.99(t, 3H), 1.20(m, 1H), 1.81(m, 2H), 2.49(s, 3H), 2.59(s, 3H), 3.65–3.90(m, 4H), 5.87(s, 1H), 7.29(d, 1H), 7.39(d, 1H), 7.51(s, 1H) | 435 |
| 39 | δ1.05(d, 3H), 1.38(d, 3H), 2.45(s, 3H), 2.56(s, 3H), 3.40(m, 2H), 5.80(s, 1H), 7.30(d, 1H), 7.37(d, 1H), 7.51(s, 1H) | 423 |
| 40 | δ0.98(t, 6H), 1.40(m, 4H), 1.75(m, 4H), 2.42(s, 3H), 2.59(s, 3H), 3.71(m, 4H), 5.76(s, 1H), 7.29(d, 1H), 7.39(d, 1H), 7.51(s, 1H) | 451 |
| 41 | δ0.29(m, 2H), 0.61(m, 2H), 0.93(t, 3H), 1.20–1.56(m, 3H), 1.75(m, 2H), 2.43(s, 3H), 2.59(s, 3H), 3.65–3.90(m, 4H), 5.88(s, 1H), 7.30(d, 1H), 7.39(d, 1H), 7.51(s, 1H) | 449 |
| 42 | δ2.42(s, 3H), 2.59(s, 3H), 4.34(t, 4H), 5.30(m, 4H), 5.87(s, 1H), 6.05(s, 1H), 7.29(d, 1H), 7.39(d, 1H), 7.51(s, 1H) | 419 |
| 43 | δ0.31(m, 2H), 0.62(m, 2H), 1.00(t, 3H), 1.23(m, 1H), 1.81(m, 1H), 2.49(s, 3H), 3.05(brs, 3H), 3.42–3.95(m, 4H), 6.04(s, 1H), 7.33(d, 1H), 7.50(s, 1H), 7.51(d, 1H) | 451 |
| 44 | δ0.13(m, 2H), 0.48(m, 2H), 0.90(t, 3H), 1.05(m, 1H), 1.60(m, 2H), 2.64(s, 3H), 3.05(brs, 3H), 3.48(d, 2H), 3.71(m, 2H), 6.04(s, 1H), 7.37(d, 1H), 7.54(s, 1H), 7.60(d, 1H) | 485 (+H₂O) |
| 45 | δ0.95(t, 3H), 1.42(m, 2H), 1.98(m, 2H), 2.49(s, 3H), 3.33(s, 3H), 3.56(m, 2H), 3.75(m, 2H), 5.93(m, 1H), 7.31(d, 1H), 7.46(s, 1H), 7.96(d, 1H), 8.40(s, 1H) | 407 |
| 46 | δ0.91(t, 3H), 0.95(t, 3H), 1.35–2.05(m, 8H), 2.70(t, 2H), 3.33(s, 3H), 3.40(m, 6H), 5.92(s, 1H), 7.30(d, 1H), 7.46(s, 1H), 8.02(d, 1H), 8.41(s, 1H) | 449 |
| 47 | δ0.87(t, 3H), 1.25(m, 2H), 1.70(m, 2H), 2.04(m, 2H), 2.68(m, 2H), 3.41(s, 3H), 3.56(m, 4H), 5.86(s, 1H), 6.60(t, 1H), 7.31(d, 1H), 7.46(s, 1H), 8.14(d, 1H), 8.50(s, 1H) | 407 |
| 48 | δ0.95(t, 6H), 1.71(m, 4H), 2.47(s, 3H), 2.55(s, 3H), 3.71(t, 4H), 5.82(s, 1H), 7.39(s, 2H), 7.70(d, 2H) | 357 |

TABLE 6-continued

Analytical data

| Co. No. | ¹H NMR data (CDCl₃) | MS M+1 |
|---|---|---|
| 49 | δ0.24(m, 2H), 0.54(m, 2H), 0.96(t, 3H), 1.12(m, 1H), 1.74(m, 2H), 2.35(s, 3H), 2.44(s, 3H), 3.73(d, 2H), 3.76(t, 2H), 5.93(s, 1H), 7.29(d, 1H), 7.35(d, 1H), 7.51(s, 1H) | 403 |
| 50 | δ1.64(t, 3H), 2.52(s, 3H), 2.60(s, 3H), 4.56(q, 2H), 6.02(s, 3H), 7.30(d, 1H), 7.37(d, 1H), 7.51(s, 1H) | 368 |
| 52 | δ0.9(t, 6H), 1.68(m, 4H), 2.13(s, 3H), 2.30(s, 3H), 2.37(s, 3H), 3.05(s, 6H), 3.65(m, 4H), 5.74(s, 1H), 6.44(s, 1H), 8.01(s, 1H) | M⁺=366 |
| 53 | δ0.9(t, 6H), 1.70(m, 4H), 2.35(s, 3H), 2.45(s, 3H), 3.05(s, 6H), 3.65(m, 4H), 5.74(s, 1H), 6.44(s, 1H), 8.01(s, 1H) | M⁺=380 |
| 54 | δ0.95(t, 6H), 1.73(m, 4H), 2.52(s, 3H), 2.76(s, 3H), 3.73(t, 4H), 5.85(s, 1H), 7.68(dd, 1H), 8.45(d, 1H), 8.57(d, 1H) | — |
| 55 | δ0.96(t, 6H), 1.70–1.78(m, 4H), 2.44(s, 3H), 2.47(s, 3H), 2.50(s, 3H), 3.73(t, 4H), 5.48(s, 1H), 8.36(d, 1H), 9.32(d, 1H) | 383 |
| 56 | δ0.93(t, 6H), 1.66–1.73(m, 4H), 2.19(s, 3H), 2.36(s, 3H), 2.42(s, 3H), 3.71(t, 4H), 5.79(s, 1H), 6.39(d, 1H), 8.05(d, 1H) | 353 |
| 57 | δ0.96(t, 6H), 1.62–1.70(m, 4H), 2.2(s, 3H), 2.36(s, 3H), 2.40(s, 3H), 2.96(s, 6H), 3.68(t, 4H), 5.76(s, 1H), 6.91(d, 1H), 8.08(d, 1H) | 381 |

TABLE 7

Analytical data

| Co. No. | Mass spectral data |
|---|---|
| 58 | 409 [M⁺] |
| 59 | 365 [M⁺] |
| 60 | 394 [MH⁺] |
| 61 | 380 [MH⁺] |
| 62 | 381 [MH⁺] |
| 63 | 381 [MH⁺] |
| 64 | 393 [MH⁺] |
| 65 | 350 [MH⁺] |
| 66 | 366 [MH⁺] |
| 67 | 381 [MH⁺] |
| 68 | 399 [MH⁺] |
| 69 | 415 [MH⁺] |
| 70 | 411 [MH⁺] |
| 71 | 399 [MH⁺] |
| 72 | 371 [MH⁺] |
| 73 | 397 [MH⁺] |
| 74 | 388 [M⁺] |
| 75 | 407 [MH⁺] |
| 76 | 373 [MH⁺] |
| 77 | 359 [MH⁺] |
| 78 | 346 [M⁺] |
| 79 | 373 [MH⁺] |
| 80 | 397 [MH⁺] |
| 81 | 381 [MH⁺] |
| 82 | 393 [MH⁺] |
| 83 | 429 [MH⁺] |
| 84 | 377 [MH⁺] |
| 85 | 409 [MH⁺] |
| 86 | 367 [MH⁺] |
| 87 | 339 [MH⁺] |
| 88 | 381 [MH⁺] |
| 89 | 367 [MH⁺] |
| 90 | 381 [MH⁺] |
| 91 | 393 [MH⁺] |
| 92 | 381 [MH⁺] |
| 93 | 409 [MH⁺] |
| 94 | 352 [MH⁺] |
| 95 | 364 [MH⁺] |
| 96 | 395 [MH⁺] |
| 97 | 407 [MH⁺] |
| 98 | 372 [MH⁺](Cl³⁵) |
| 99 | 464 [MH⁺] |
| 100 | 356 [MH⁺] |
| 101 | 426 [MH⁺](Cl³⁵) |
| 102 | 458 [MH⁺](Cl³⁵) |
| 103 | 392 [MH⁺](Cl³⁵) |
| 104 | 408 [MH⁺](Cl³⁵) |
| 105 | 404 [MH⁺](Cl³⁵) |
| 106 | 368 [MH⁺] |
| 107 | 409 [MH⁺] |
| 108 | 421 [MH⁺] |
| 109 | 383 [MH⁺] |
| 110 | 353 [MH⁺] |
| 111 | 372 [MH⁺](Cl³⁵) |
| 112 | 366 [MH⁺] |
| 113 | 381 [MH⁺] |
| 114 | 338 [MH⁺] |
| 115 | 377 [MH⁺] |
| 116 | 383 [MH⁺] |
| 117 | 399 [MH⁺] |
| 118 | 395 [MH⁺] |
| 119 | 415 [MH⁺] |
| 120 | 385 [MH⁺] |
| 121 | 367 [MH⁺] |
| 122 | 383 [MH⁺] |
| 123 | 383 [MH⁺] |
| 124 | 399 [MH⁺] |
| 125 | 338 [MH⁺] |
| 126 | 353 [MH⁺] |
| 127 | 365 [MH⁺] |
| 128 | 370 [M⁺] |
| 129 | 368 [M⁺] |
| 130 | 393 [MH⁺] |
| 131 | 379 [MH⁺] |

C. Pharmacological examples

EXAMPLE C.1

Representative Compounds having CRF Receptor Binding Activity

Compounds were evaluated for binding activity to the CRF receptor by a standard radioligand binding assay as generally described by DeSouza et al. (J. Neurosci. 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay was performed in 1.5 ml Eppendorf tubes using approximately 1×10⁶ cells per tube stably transfected with human CRF receptors. Each tube received about 0.1 ml of assay buffer (e.g., Dulbecco's phosphate buffered saline, 10 mM magnesium chloride, 20 μM bacitracin) with or without unlabeled sauvagine, urotensin I or CRF (final concentration, 1 μM) to determine nonspecific binding, 0.1 ml of [¹²⁵I]tyrosine—ovine CRF (final concentration ~200 pM or approximately the $K_D$ as determined by Scatchard analysis) and 0.1 ml of a membrane suspension of cells containing the CRF receptor. The mixture was incubated for 2 hours at 22° C. followed by the separation of the bound and free radioligand by centrifugation. Following two washes of the pellets, the tubes were cut just above the pellet and monitored in a gamma counter for radioactivity at approximately 80% efficiency. All radioligand binding data was analyzed using a non-linear least-square curve-fitting program.

Binding activity corresponds to the concentration (nM) of the compound necessary to displace 50% of the radiolabeled ligand from the receptor. The following compounds have a $K_i \leq 250$ nM :5, 10, 12, 15–17, 19, 23, 24, 26, 27, 29, 31–33, 36–43, 48, 49, 51–54 and 57–130 as listed in Tables 2–5. Compounds 17, 29, 38, 41, 42, 48, 49, 51–54, 57, 58, 70, 71, 81–85, 90–92, 101, 103–105, 115, 118, 121–123 and 125 were found to show the best score in this test.

EXAMPLE C.2

CRF Stimulated Adenylate Cyclase Activity

The compounds of the present invention may also be evaluated by various functional testing. For example, the compounds of the present invention may be screened for CRF-stimulated adenylate cyclase activity. An assay for the determination of CRF-stimulated adenylate cyclase activity may be performed as generally described by Battaglia et al. (Synapse 1:572, 1987), with modifications to adapt the assay to whole cell preparations.

More specifically, the standard assay mixture may contain the following in a final volume of 0.5 ml: 2 mM L-glutamine, 20 mM HEPES, and 1 mM IMBX in DMEM buffer. In stimulation studies, whole cells with the transfected CRF receptors are plated in 24-well plates and incubated for 1 hour at 37° C. with various concentrations of CRF-related and unrelated peptides in order to establish the pharmacological rank-order profile of the particular receptor subtype. Following the incubation, the medium is aspirated, the wells rinsed once gently with fresh medium, and the medium aspirated. To determine the amount of intracellular cAMP, 300 µl of a solution of 95% ethanol and 20 mM aqueous hydrochloric acid is added to each well and the resulting suspensions are incubated at −20° C. for 16 to 18 hours. The solution is removed into 1.5 ml Eppendorf tubes and the wells washed with an additional 200 µl of ethanol/aqueous hydrochloric acid and pooled with the first fraction. The samples are lyophilized and then resuspended with 500 µl sodium acetate buffer. The measurement of cAMP in the samples is performed using a single antibody kit. For the functional assessment of the compounds, a single concentration of CRF or related peptides causing 80% stimulation of cAMP production is incubated along with various concentrations of competing compounds ($10^{-12}$ to $10^{-6}$M).

EXAMPLE C.3

The plus-maze and defensive withdrawal paradigms are correlated measures of exploratory activity sensitive to anxiogenic and anxiolytic effects of experimental treatments. These animal models are employed to examine anxiolytic and anti-stress actions of compounds of the present invention.

EXAMPLE C.3-a

The Elevated Plus-Maze Paradigm

This test predicts how animals respond to an approach-avoidance situation involving a bright lighted space versus a dark "safe" area. Both spaces are elevated off the ground and constitute two runways intersecting in the form of plus sign. This type of approach-avoidance situation is a classical test of "emotionality" and reactivity and is very sensitive to treatments that produce disinhibition (such an sedative/hypnotic drugs) and stress. No motivational constraints are necessary and the animal is free to remain in the dark or venture out on the open arms. The plus-maze apparatus has four arms (10×50 cm) at right angles to each other and is elevated from the floor (50 cm). Two of the arms are enclosed with walls (40 cm high) and two arms have no walls (open arms). Subjects are placed individually onto the center of the maze and allowed free access to all four arms for 5 minutes. Subjects are observed through a window in the door and via an on-line display of the rat's location on a computer monitor. Time spent in each arm is recorded automatically by photocell beams and a computer program. The maze is wiped clean with a damp cloth between each trial. The measure of anxiogenic-like behavior in this task is a decrease in time spent on open arms while the measure of anti-stress efficacy is a complementary increase in time spent on open arms.

Validation of the Plus-Maze Using CRF Peptides

Central administration of CRF and exposure to any of several experimental stressors suppresses exploration in the elevated plus maze model of anxiety. When measuring the behavioral response to social defeat, central administration of the alpha-helical CRF (9–41) antagonist either post-stress [25 µg ICV] or pre-stress [1 µg ICV] reverses the anxiogenic effect of social defeat. This anti-stress action of the CFR antagonist is also exerted following intracerebral administration into the central nucleus of amygdala [250 ng IC].

Rats were administered the test compounds orally one hour prior to the five minute test. Some groups were placed in a water-filled pool for ninety seconds immediately prior to placement on the Plus-Maze (Stress group) while control subjects were removed directly from the home cage (Non-Stress group). In the non-treated animal group a significant reduction of the percentage of the average time spent in the open arms was observed (from about 36 to about 16 %). Upon administration of 2.5 or 20 mg/kg of compound 53, the % time in the open arms returned to a level equal, within the error range, to the untreated group.

EXAMPLE C.3-b

The defensive Withdrawal Paradigm

Testing takes place in a plexiglas open field (106×92×77 cm) containing a cylindrical galvanized steel chamber measuring 17.1 cm deep and 10.2 cm in diameter. The chamber is open at one end and is located along the wall of the open field aligned lengthwise and 15.0 cm away from a corner of the open field. The open end faces the corner. The open field is illuminated by fluorescent ceiling lighting. For testing, the animals are introduced into the unfamiliar test environment by placing them into the small chamber. Tests take 5 minutes in duration and the apparatus is cleaned with a mild acetic acid solution after each test. The test compound is administered orally one hour before the 5 minutes test. The behavior of the animals is monitored and recorded by video camera. The latency to leave the chamber will be measured and defined as the placement of all four paws in the open field. Also measured is the number of passages made between the chamber and the open field and the average length of time in the chamber per entry. The measure of anxiolytic efficacy is a decrease in mean time spent within the enclosed chamber. Compound 53 reduced the mean time in the chamber from about 80 seconds to about 20 to 40 seconds when administered at doses of 0.63, 2.5 and 20 mg/kg p.o. to rats.

Validation of Defensive Withdrawal using CRF peptides

When injected ICV, both alpha-helical CFR (9–41) and CRF modify behavior in the defensive withdrawal paradigm. In particular, ICV administration of CRF in animals previously familiarized with the apparatus increases both the latency to emerge from the small chamber and mean time spent in the chamber over the fifteen minute session. Similarly, infusion of CRF into the locus ceruleus produced similar changes in defensive withdrawal behavior suggesting that the interaction of CRF with noradrenergic neurons is involved in defensive withdrawal behavior in rats. Conversely, ICV administration of alpha-helical CRF (9–14) or d-Phe CR-F (12–41), competitive CRF receptor antagonists, reverses the CRF-like effect of a restraint stressor in familiar environment condition and significantly decreases latency to emerge and mean time in chamber measures in animals unfamiliar with the apparatus.

D. Composition examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a N-oxide form, a pharmaceutically acceptable acid or base addition salt or a stereochemically isomeric form thereof.

EXAMPLE D.1

Oral solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE D.2

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I..

EXAMPLE D.3

Film-coated tablets

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension and the whole is homogenated. The tablet cores are coated with the thus obtained mixture in a coating apparatus.

EXAMPLE D.4

Injectable solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration and filled in sterile containers.

EXAMPLE D.5

Suppositories

3 Grams A.I. was dissolved in a solution of 3 grams 2,3-dihydroxybutanedioic acid in 25 ml polyethylene glycol 400. 12 Grams surfactant and 300 grams triglycerides were molten together. The latter mixture was mixed well with the former solution. The thus obtained mixture was poured into moulds at a temperature of 37 to 38° C. to form 100 suppositories each containing 30 mg/ml of the A.I.

What is claimed is:

1. A compound of formula

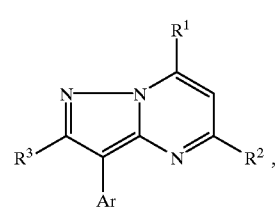

(I)

including the stereoisomers and the pharmaceutically acceptable acid addition salt forms thereof, wherein
$R^1$ is $NR^4R^5$ or $OR^5$;
$R^2$ is $C_{1-6}$alkyl, $C_{1-6}$alkyloxy or $C_{1-6}$alkylthio;
$R^3$ is hydrogen, $C_{1-6}$alkyl, $C_{1-6}$alkylsulfonyl, $C_{1-6}$alkylsulfoxy or $C_{1-6}$alkylthio;
$R^4$ is hydrogen, $C_{1-6}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl;
$R^5$ is $C_{1-8}$alkyl, mono- or di($C_{3-6}$cycloalkyl)methyl, $Ar^1CH_2$, $C_{3-6}$alkenyl, $C_{1-6}$alkyloxy$C_{1-6}$alkyl, hydroxy$C_{1-6}$alkyl, thienylmethyl, furanylmethyl, $C_{1-6}$alkylthio$C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of formula —Alk—O—CO—$Ar^1$;
or $R^4$ and $R^5$ taken together with the nitrogen atom to which they are attached may form a piperidinyl, homopiperidinyl or morpholinyl group, optionally substituted with $C_{1-6}$alkyl or $C_{1-6}$alkyloxy$C_{1-6}$alkyl; and Ar is phenyl substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl)amino; pyridinyl; pyridinyl substituted with 1, 2 or 3 substituents independently selected from halo, $C_{1-6}$alkyl, trifluoromethyl, hydroxy, cyano, $C_{1-6}$alkyloxy, benzyloxy, $C_{1-6}$alkylthio, nitro, amino, mono- or di($C_{1-6}$alkyl)amino and piperidinyl; and wherein said substituted phenyl may optionally be further substituted with one or more halogens;

$Ar^1$ is phenyl; phenyl substituted with 1, 2 or 3 substituents each independently selected from halo, $C_{1-6}$alkyl, $C_{1-6}$alkyloxy, di($C_{1-6}$alkyl)amino$C_{1-6}$alkyl, trifluoromethyl and $C_{1-6}$alkyl substituted with morpholinyl; or pyridinyl; and Alk is $C_{1-6}$alkanediyl.

2. A compound according to claim 1 wherein $R^1$ is $OR^5$ and $R^5$ is $C_{1-6}$alkyl; or $R^1$ is $NR^4R^5$ and $R^4$ is hydrogen, $C_{1-6}$alkyl, hydroxy$C_{1-6}$alkyl, $C_{1-6}$alkylcarbonyloxy-$C_{1-6}$alkyl or $C_{3-6}$alkenyl, $R^5$ is $C_{1-8}$alkyl, $C_{3-6}$alkenyl, hydroxy$C_{1-6}$alkyl, $C_{1-6}$alkyloxy$C_{1-6}$alkyl, phenylmethyl or $C_{3-6}$cycloalkylmethyl; or $R^4$ and $R^5$ are taken together with the nitrogen atom to which they are attached to form a piperidinyl, homopiperidinyl or morpholinyl group, optionally substituted with $C_{1-6}$alkyl or $C_{1-6}$alkyloxy$C_{1-6}$alkyl; $R^2$ is $C_{1-6}$alkyl; $R^3$ is hydrogen, $C_{1-6}$alkyl or $C_{1-6}$alkylthio; and Ar is a phenyl substituted with 1, 2 or 3 substituents each independently selected from halo, $C_{1-6}$alkyl or $C_{1-6}$alkyloxy; or Ar is a pyridinyl substituted with 1, 2 or 3 substituents each independently selected from halo, amino, nitro, trifluoromethyl, mono- or di($C_{1-6}$alkyl)amino, piperidinyl or $C_{1-6}$alkyl.

3. A compound according to claim 1 wherein $R^1$ is $NR^4R^5$ and $R^4$ is $C_{2-4}$alkyl, hydroxy$C_{1-2}$alkyl, $C_{3-4}$alkenyl or $C_{1-2}$alkylcarbonyloxy$C_{2-4}$alkyl; $R^5$ is $C_{2-4}$alkyl, $C_{3-4}$alkenyl, hydroxy$C_{2-4}$alkyl or cyclopropylmethyl; $R^2$ is $C_{1-2}$alkyl; $R^3$ is hydrogen, $C_{1-2}$alkyl or $C_{1-2}$alkylthio.

4. A compound according to claim 1 wherein $R^1$ is $NR^4R^5$ and $R^4$ is $C_{3-4}$alkyl or allyl; $R^5$ is $C_{2-4}$alkyl, allyl or cyclopropylmethyl; $R^2$ is methyl; $R^3$ is methyl; and Ar is phenyl substituted in the 3-, 4-, 6-, 2,4- or 2,4,6-positions with halo, $C_{1-6}$alkyl or $C_{1-6}$alkyloxy.

5. A compound according to claim 1 wherein $R^1$ is $NR^4R^5$ and $R^4$ is $C_{3-4}$alkyl or allyl; $R^5$ is $C_{3-4}$alkyl, allyl or cyclopropylmethyl; $R^2$ is methyl; $R^3$ is methyl; and Ar is 3-pyridinyl substituted on the 4- and/or 6-position with methyl or dimethylamino.

6. A compound according to claim 1 wherein the compound is 3-[6-(dimethylamino)-3-pyridinyl]-2,5-dimethyl-N,N-dipropylpyrazolo[2,3-a]pyrimidin-7-amine, or 3-[6-(dimethylamino)-4-methyl-3-pyridinyl]-2,5-dimethyl-N,N-dipropylpyrazolo[2,3-a]pyrimidin-7-amine;

the stereochemically isomeric forms, or the pharmaceutically acceptable acid addition salts thereof.

7. A composition comprising a pharmaceutically acceptable carrier, and as active ingredient a therapeutically effective amount of a compound as claimed in any one of claims 1 to 6 or 14.

8. A process for preparing a composition as claimed in claim 7 characterized in that a therapeutically effective amount of the compound is intimately mixed with a pharmaceutically acceptable carrier.

9. A method of treating endocrine, psychiatric or neurologic disorders or illnesses in a warm-blooded animal comprising administering to said animal in need of treatment a therapeutically effective amount of the compound according to any of claims 1 to 6 or 14.

10. The compound according to claim 1 wherein $R^1$ is $NR^4R^5$.

11. The compound according to claim 2 wherein $R^1$ is $NR^4R^5$ and $R^4$ is $C_{2-4}$alkyl, hydroxy$C_{1-2}$alkyl, $C_{3-4}$alkenyl or $C_{1-2}$alkylcarbonyloxy $C_{2-4}$alkyl; $R_5$ is $C_{2-4}$alkyl, $C_{3-4}$alkenyl, hydroxy$C_{2-4}$alkyl or cyclopropylmethyl; $R^2$ is $C_{1-2}$alkyl; and $R^3$ is hydrogen, $C_{1-2}$alkyl or $C_{1-2}$alkylthio.

12. A method for treating a physiological condition or disorder in a warm-blooded animal arising from the hypersecretion of corticotropin-releasing factor comprising administering to said animal an effective amount of a compound of the formula

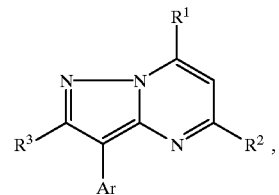

(I)

including the stereoisomers and the pharmaceutically acceptable acid addition salt forms thereof, wherein $R^1$ is $NR^4R^5$ or $OR^5$;

$R^2$ is $C_{1-6}$alkyl, $C_{1-6}$alkyloxy or $C_{1-6}$alkylthio;

$R^3$ is hydrogen, $C_{1-6}$alkyl, $C_{1-6}$alkylsulfonyl, $C_{1-6}$alkylsulfoxy or $C_{3-6}$cycloalkyl;

$R^4$ is hydrogen, $C_{1-6}$alkyl, mono- or di($C_{3-6}$cycloalkyl)methyl, $C_{3-6}$cycloalkyl, $C_{3-6}$alkyenyl, hydroxy$C_{1-6}$alkyl, $C_{1-6}$alkylcarbonyloxy$C_{1-6}$alkyl or $C_{1-6}$alkyloxy$C_{1-6}$alkyl;

$R^5$ is $C_{1-8}$alkyl, mono-or di($C_{3-6}$cycloalkyl)methyl, $Ar^1CH_2$, $C_{3-6}$alkenyl, $C_{1-6}$alkyloxy$C_{1-6}$alkyl, hydroxy$C_{1-6}$alkyl, thienylmethyl, furanylmethyl, $C_{1-6}$alkylthio$C_{1-6}$alkyl, morpholinyl, mono- or di($C_{1-6}$alkyl)amino$C_{1-6}$alkyl, di($C_{1-6}$alkyl)amino, $C_{1-6}$alkylcarbonyl$C_{1-6}$alkyl, $C_{1-6}$alkyl substituted with imidazolyl; or a radical of formula —Alk—O—CO—$Ar^1$;

or $R^4$ and $R^5$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl;

Ar is phenyl; phenyl substituted with 1, 2 or 3 substituents independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl)amino; pyridinyl; pyridinyl substituted with 1, 2 or 3 substituents independently selected from the group consisting of halo, $C_{1-6}$alkyl, trifluoromethyl, hydroxy, cyano, $C_{1-6}$alkyloxy, benzyloxy, $C_{1-6}$alkylthio, nitro, amino, mono- or di($C_{1-6}$alkyl)amino and piperidinyl; and wherein said substituted phenyl may optionally be further substituted with one or more halogens;

$Ar^1$ is phenyl; phenyl substituted with 1, 2 or 3 substituents each independently selected from the group consisting of halo, $C_{1-6}$alkyl, $C_{1-6}$alkyloxy, di($C_{1-6}$alkyl) amino$C_{1-6}$alkyl, trifluoromethyl and $C_{1-6}$alkyl substituted with morpholinyl; or pyridinyl; and Alk is $C_{1-6}$alkanediyl.

13. The method according to claim 12 wherein said compound is 5-methyl-3-phenyl-7-(phenylmethoxy)- pyrazolo [1,5-a]pyrimidine or 2,5-dimethyl-7-(methylamino)-3-phenylpyrazolo-[1,5a]pyrimidine.

14. A method for inhibiting a CRF receptor in a warm blooded animal comprising administering the compound according to claim 1 in an amount effective to antagonize said CRF receptor.